United States Patent [19]

Horwath et al.

[11] Patent Number: 4,463,093

[45] Date of Patent: Jul. 31, 1984

[54] PROCESS FOR ISOMERIZING L-GLUCOSE TO L-FRUCTOSE

[75] Inventors: Robert O. Horwath, Westport; William J. Colonna, Wilton, both of Conn.

[73] Assignee: Nabisco Brands, Inc., Parsippany, N.J.

[21] Appl. No.: 393,846

[22] Filed: Jun. 30, 1982

[51] Int. Cl.$^3$ .......... C12P 19/24; C12N 9/92; C12R 1/72
[52] U.S. Cl. .......... 435/94; 435/234; 435/921
[58] Field of Search .......... 435/94, 233, 234, 921

[56] References Cited

U.S. PATENT DOCUMENTS 2,950,228  8/1960  Marshall .......... 435/94
3,689,362  9/1972  Takasaki .......... 435/234

OTHER PUBLICATIONS

Tomoyeda et al., Agr. Biol. Chem., vol. 28, No. 3, pp. 139-143, 1964.
Enzyme Nomenclature, 1978, pp. 418-419.

*Primary Examiner*—Lionel M. Shapiro
*Attorney, Agent, or Firm*—Richard Kornutik

[57] ABSTRACT

Process for preparing L-fructose from L-glucose by contacting L-glucose with xylose isomerase produced by a microorganism of the genus Candida.

2 Claims, No Drawings

PROCESS FOR ISOMERIZING L-GLUCOSE TO L-FRUCTOSE

BACKGROUND OF THE INVENTION

This invention relates to a process for preparing L-fructose alone or in admixture with other L-sugars, such as L-glucose.

L-sugars are useful as sweetening agents because, as disclosed in U.S. Pat. No. 4,262,032, they are sweet like the D-sugars, but unlike D-sugars, L-sugars are either not metabolized by the body or are metabolized to a lesser extent than the D-sugars. These features make L-sugars desirable as sweeteners for individuals wishing to reduce caloric-intake or for individuals unable to metabolize common sugar sweetening agents without detrimental effects, e.g., diabetics. Another advantage associated with L-sugars is the absence of an objectionable aftertaste commonly experienced with artificial sweeteners such as saccharin and the cyclamates. However, as desirable as the L-sugars are in the foregoing respects, their relative scarcity in nature, particularly L-glucose and L-fructose, the laevo counterparts of the two monosaccharide sweeteners most commonly used today, has prevented their widespread use in foods and beverages.

Tomoyeda, et al., "Pentose Metabolism by *Candida utilis*," Agr. Biol. Chem., Vol. 28, No. 3, pp. 139–143 (1964), the contents of which are incorporated by reference herein, describes the enzymatic isomerization of D- and L-xylose to the respective ketopentoses by employing xylose isomerase isolated from *Candida utilis* acclimatized on xylose medium.

SUMMARY OF THE INVENTION

In accordance with the present invention, L-glucose is isomerized to L-fructose by employing xylose isomerase isolated from or present in a strain of microorganism of the genus Candida. It has been found that due to the low stereospecificity of the xylose isomerase produced by, for example, *Candida utilis*, said isomerase also isomerizes L-glucose to L-fructose. The isomerization reaction is reversible and reaches an equilibrium state.

To increase the yield of L-fructose, a borate compound is added to the reaction system, preferably at the beginning of the isomerization process, which selectively complexes with L-fructose to remove the L-fructose from the reaction system. Accordingly, the equilibrium shifts, resulting in higher yields of L-fructose.

A procedure for increasing the D-fructose yield in the enzymatic isomerization of D-glucose employing glucose isomerase in the presence of a borate compound is described in U.S. Pat. No. 3,689,362 to Takasaki, the contents of which are incorporated by reference herein.

DESCRIPTION OF THE PREFERRED EMBODIMENTS

The starting L-sugar for the process herein, L-glucose, a scarce, naturally occurring sugar, can be obtained by chemical conversion of L-arabinose, a naturally occurring sugar which is available in significant quantities from sugar beet pulp by the method described in Chemical Abstracts: 142135v, Vol. 75, 1971 (Czech. Pat. No. 137,537), the contents of which are incorporated by reference herein. According to this method, dry sugar beet pulp is treated with sulfuric acid to obtain an extract solution which is subsequently fermented, evaporated and filtered. L-arabinose is thereafter crystallized from the resulting filtrate.

L-glucose can be produced from L-arabinose by the method of Sowden and Fischer, J.A.C.S., Vol. 69 (1947), pp. 1963–1965. In accordance with this method, L-arabinose is condensed with nitromethane in the presence of sodium methoxide to provide sodium salts of the nitroalcohols. The sodium salts are readily converted to the corresponding sugars by means of the Nef reaction. The Sowden-Fischer conversion of L-arabinose to the L-glucose starting material of this invention is represented by the following equations:

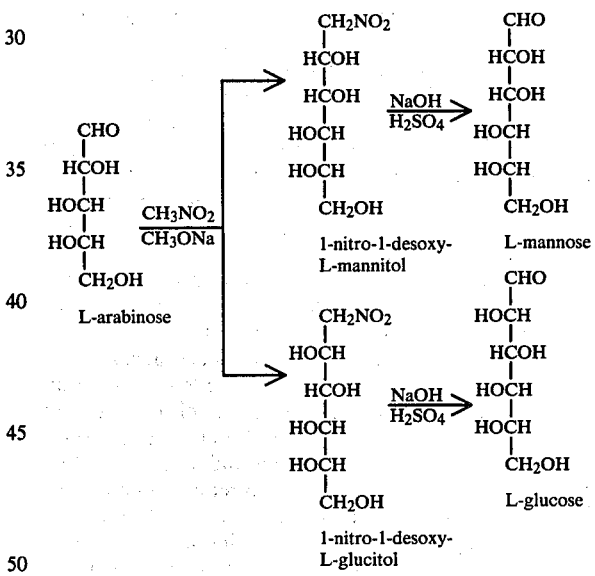

In addition to the Sowden-Fischer method, L-glucose can also be made by the Kiliani-Fischer synthesis which is described in, amongst others, Organic Chemistry by Morrison and Boyd (2d ed. 1966), pp. 990–991, the contents of which are incorporated by reference herein. According to the Kiliani-Fischer method, L-arabinose is converted into two glyconic acids of the next higher carbon number by condensation with hydrocyanic acid and hydrolysis of the resulting cyanohydrins. The glyconic acids are then reduced to the corresponding aldoses. The Kiliani-Fischer synthesis of L-glucose from L-arbinose is illustrated by the following equations:

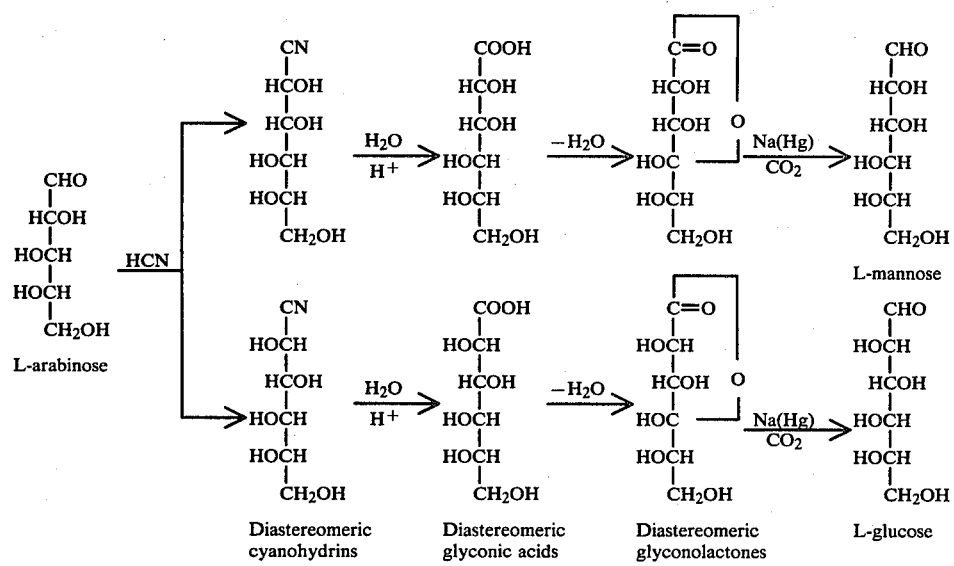

Both synthetic procedures provide L-glucose in admixture with L-mannose. The L-glucose can be separated from the L-mannose, e.g., by differential crystallization in either a free or derivatized state, or by separation using ion-exchange techniques.

To obtain the xylose isomerase utilized herein, a strain of *Candida utilis* is cultivated under aerobic conditions at a temperature within the range of 25° C. to 35° C., preferably 25° C. to 30° C., with shaking for about ten to forty-eight hours in a medium containing xylose, glucose, polypeptone and a trace of $MnCl_2$ at a pH within the range of 5 to 8, preferably between 5 and 6.

The freshly cultured cells are thereafter harvested by known techniques, e.g., supercentrifugation, and washed in distilled water.

The L-glucose isomerization is carried out by utilizing art recognized procedures to immobilize the cells containing xylose isomerase or to rupture the cells, for example, through plasmolysis by butyl acetate, or through ultra-sonic treatment. If the cells are ruptured to release the intracellular isomerase, a cell-free extract containing the enzyme is obtained by known methods, e.g., centrifugation, and the extract dialyzed in distilled water at 2° C. over twenty hours to remove impurities. The dialyzed solution can be further purified by methods generally known in the art, including ammonium sulfate fractionation. The extracellular enzyme can be immobilized in accordance with known and conventional procedures. For example, the enzyme can be immobilized on various particulate silica material including glass or ceramic-based materials, natural or synthetic polymers such as cellulose, e.g., diethylaminoethyl cellulose, and various other known organic polymer supports known in the art.

The substrate is added to the reaction mixture, and the isomerization process is carried out at about 30° C. for a length of time which can be readily determined experimentally. The isomerization reaction can be conducted at temperatures up to 70° C., the optimum temperature, and even higher but with possible loss of enzyme activity. The enzyme can be protected against the heat treatment by addition of metal cations, e.g., manganese ion, to the reaction system. The reaction temperature selection will be predicted on the thermal stability of the enzyme system employed, the more thermally stable systems permitting higher reaction temperatures. Of course, the reaction time will, in part, be determined by the reaction temperature. As would be expected, the higher the temperature, the shorter the reaction time period for the desired degree of reaction. In enzymatic reactions of the present type, equilibrium will be reached in reasonable time periods, usually ranging from as little as 30 minutes up to several hours, and even longer. As is recognized in this art, the progress of the reaction can be followed by removal of aliquots from the reaction mixture and analyzing for product and/or starting substrate, thus, permitting optimization of reaction parameters for the specific enzyme system employed. The enzyme system may vary depending on the microorganism from which the enzyme is obtained, and the method of isolation and purification, if employed.

Once equilibrium is established, the isomerization reaction is essentially completed and the enzyme is removed from the reaction mixture by art recognized procedures, e.g., by denaturing the enzyme and removing the denatured protein by centrifugation, or separation of immobilized enzyme by physical means, e.g., filtration.

In a preferred embodiment of the present invention, a borate compound which selectively complexes with L-fructose is added to a reaction mixture containing L-glucose, phosphate buffer at pH 5.5, $5 \times 10^{-3}M$ $MnCl_2$, and enzyme solution. Suitable borate compounds are water-soluble borates, such as sodium or potassium borate, and water-insoluble or slightly soluble borates, such as magnesium and barium borate. Anion-exchange resins in the borate form can also be used in this invention. To obtain the maximum isomerization ratio, an optimum concentration of borate to be added can be determined experimentally. Factors to be taken into consideration in determining the optimum concentration include the L-glucose concentration and the type of borate selected. Since the borate compound forms a borate-sugar complex with L-fructose, L-fructose is removed from the reaction system, and the isomerization equilibrium shifts to produce greater quantities of L-fructose.

The reaction mixture is then incubated at 70° C. for thirty minutes, or until equilibrium is reached. Subsequently, the enzyme is removed from the reaction mixture by denaturing the protein and removing the denatured protein by centrifugation.

L-fructose is recovered from the borate-sugar complex by heating the solution with a cation-exchange resin, or with a mineral acid to bring the pH of the solution to below 3. Since the borate-sugar complex is unstable under acidic conditions, particularly when the solution temperature is reduced to below about 10° C., the borate compound decomposes into boric acid and the corresponding inorganic salt, and the boric acid precipitates from the solution. Any residual boric acid and the dissolved inorganic salt can be separated from the L-fructose-L-glucose solution by methods known in the art, e.g., ion-exchange techniques, electrodialysis, and distillation.

L-fructose in admixture with unreacted L-glucose can be used as a sweetening agent or, if desired, the two L-sugars can be separated by known techniques, e.g. by differential crystallization or by ion-exchange columns.

EXAMPLE

A. Isolation of xylose isomerase

Cells of *Candida utilis* are cultivated for forty-eight hours at 28° C. on reciprocal shakers in an aqueous medium containing 2% xylose, 0.5% glucose, 0.5% polypeptone and 0.005% $MnCl_2$ at pH 5.5.

The freshly cultivated cells are harvested by centrifugation, washed twice with distilled water, and plasmolyzed by butyl acetate. Cellular debris is then removed by centrifugation and the remaining extract is dialyzed in distilled water at 2° C. over twenty hours to remove impurities. After dialysis, the extract is centrifuged to remove the impurities.

The enzyme extract is further purified by using ammonium sulfate fractionation. The dialyzed solution is treated with ammonium sulfate to 30% saturation, then to 50% saturation, and finally to 80% saturation. Each precipitate is dissolved and any insoluble residue removed by centrifugation. Each fraction is assay tested for enzyme activity.

The fraction containing enzyme activity is further purified by fractionation with acetone and by means of adsorption to calcium phosphate gel. Said fraction is dissolved in sufficient distilled water to provide a protein content therein of 1.5 mg per ml, and fractionation with acetone is carried out by adding acetone to 50% concentration, and then to 75% concentration. After determining which precipitate-fraction has enzyme activity, sufficient phosphate buffer (pH 7.5) is added to said fraction to make the protein content therein 10 mg per ml. and calcium phosphate gel is added to the suspension. After centrifugation of the resulting mixture, a gel containing the enzyme is obtained. The gel is eluted with 0.1M phosphate buffer (pH 6.0), and the eluate is immediately treated with ammonium sulfate to 80% saturation. The final precipitate is collected by centrifugation.

B. Isomerization of L-glucose to L-fructose

The reaction mixture containing 50 mmoles of L-glucose, (phosphate buffer at pH 5.5), $5 \times 10^{-3}$M $MnCl_2$ and enzyme solution (50 mg of protein) is incubated at 37° C. for 12 to 18 hours, or until equilibrium is established. The reaction mixture is then heated in a boiling water bath, and the denatured protein removed by centrifugation.

While the present invention has been described in connection with specific embodiments thereof, it is understood that it is capable of further modifications and adaptations as will be readily understood by those skilled in the art.

We claim:

1. A process for isomerizing L-glucose to L-fructose which comprises contacting L-glucose with xylose isomerase of low stereospecificity produced by a microorganism of the genus Candida.

2. A process according to claim 1, wherein the microorganism is *Candida utilis*.

* * * * *